United States Patent
Ma et al.

(10) Patent No.: US 8,454,596 B2
(45) Date of Patent: Jun. 4, 2013

(54) ELECTROPHYSIOLOGY ABLATION DEVICE

(75) Inventors: Xiaoyi Ma, Beijing (CN); Congxin Huang, Beijing (CN); Zhengyang Li, Beijing (CN)

(73) Assignee: Beijing Amsino Medical Co., Ltd., Beijing (CN)

( * ) Notice: Subject to any disclaimer, the term of this patent is extended or adjusted under 35 U.S.C. 154(b) by 700 days.

(21) Appl. No.: 12/672,872

(22) PCT Filed: Aug. 10, 2007

(86) PCT No.: PCT/CN2007/070451
§ 371 (c)(1),
(2), (4) Date: Apr. 8, 2010

(87) PCT Pub. No.: WO2009/021378
PCT Pub. Date: Feb. 19, 2009

(65) Prior Publication Data
US 2010/0256627 A1    Oct. 7, 2010

(51) Int. Cl.
*A61B 18/14* (2006.01)
(52) U.S. Cl.
USPC ............................................................ 606/41
(58) Field of Classification Search
USPC ................................................ 606/27, 34, 41
See application file for complete search history.

(56) References Cited

U.S. PATENT DOCUMENTS

| | | | |
|---|---|---|---|
| 5,738,683 A | 4/1998 | Osypka | |
| 5,820,629 A | 10/1998 | Cox | |
| 5,836,947 A | 11/1998 | Fleischman et al. | |
| 6,315,778 B1 * | 11/2001 | Gambale et al. | 606/41 |
| 6,592,612 B1 * | 7/2003 | Samson et al. | 607/105 |
| 6,837,886 B2 | 1/2005 | Collins et al. | |
| 6,893,438 B2 | 5/2005 | Hall et al. | |
| 7,013,169 B2 * | 3/2006 | Bowe | 600/374 |

FOREIGN PATENT DOCUMENTS

| | | |
|---|---|---|
| CN | 1700880 A | 11/2005 |
| CN | 1747810 A | 4/2007 |
| CN | 1966104 A | 5/2007 |
| EP | 2184025 B1 | 11/2012 |
| JP | 6296694 | 10/1994 |
| WO | WO0117451 A1 | 3/2001 |
| WO | WO0182814 A2 | 11/2001 |

OTHER PUBLICATIONS

International Search Report and Written Opinion mailed May 15, 2008 for PCT/CN2007/070451.

(Continued)

*Primary Examiner* — Michael Peffley
*Assistant Examiner* — Daniel Fowler
(74) *Attorney, Agent, or Firm* — Schwabe, Williamson & Wyatt, P.C.

(57) ABSTRACT

An electrophysiology ablation device includes a catheter sleeve (1), an electrode sleeve (2), a steering ball sleeve (4), a central rod (6), an ablation electrode (3) and a steering ball (5). The catheter sleeve (1), the electrode sleeve (2), the steering ball sleeve (4) and the central rod (6) are muff-coupled together, and the steering ball (5) can be deployed radially to define a meshed spherical shape, in order to steer the positioning of the ablation electrode (3) which can be deployed to define a meshed disk shape, so the ablation electrode (3) can be positioned at the ostium of the pulmonary vein accurately.

10 Claims, 4 Drawing Sheets

OTHER PUBLICATIONS

Extended European Search Report mailed Sep. 24, 2010 for EP 07800927.1.

Office Action mailed Feb. 1, 2012 for JP 2010-519323.

Decision of Rejection based on Office Action mailed Feb. 1, 2012 for JP 2010-519323.

* cited by examiner

ELECTROPHYSIOLOGY ABLATION DEVICE

CROSS REFERENCE TO RELATED APPLICATIONS

The present application is the U.S. National Stage of International Application No. PCT/CN2007/070451, filed Aug. 10, 2007.

FIELD OF THE INVENTION

The present invention relates to electrophysiologically therapeutic device for the treatment of arrhythmia in the field of medical appliances, and more particularly, to an electrophysiology ablation device.

BACKGROUND OF THE RELATED ART

The heart is a complicated organ. Stimulation by heart current causes myocardial contraction to pump out blood and makes the blood to circulate in the blood vessel. The heart current passes through the atrium and then the ventricle to cause myocardial contraction. The myocardium rhythmically contracts under the action of heart current. However, the advance in age or the change in pathological and physiological characteristics of the heart causes contraction disorder and abnormal rhythm of the heart. One of the methods to treat arrhythmia is septal ablation, that is, making the abnormal heart current loop open through an interventional surgery. To perform ablation, it is necessary to guide the catheter with an ablation electrode to reach the left atrium. This is usually performed by femoral artery puncture, whereby the electrophysiology catheter with an ablation electrode is delivered to the left atrium under X-ray image observation, the electrode is placed against the orifice of the pulmonary vein, the site of abnormal heart current loop that generates arrhythmia is determined by collecting electric signals, and the discharge energy or other energy generated by the ablation electrode brings about lesion degeneration or coagulative necrosis to the tissue near this site, to thereby cut off the abnormal heart current loop. The energy for use in ablation can be radio frequency current, direct current, microwave, ultrasonic wave or laser.

The key to electrophysiology ablation is positioning of the electrode, namely to determine the site to be ablated in a quick and precise manner. U.S. Pat. No. 6,837,886 B2 proposes an electrophysiology ablation device, whose positioning method is carried out by an openable meshed flat disk concealed in the catheter head. During the process of vein puncture, the disk is concealed in the catheter head, and after the catheter head is inserted into the orifice of the pulmonary vein, the disk is opened to abut against the orifice of the pulmonary vein. The disk is braided from a metal wire, which has electrically conductive function, and is itself an electrode that generates electric pulses once the power is on to carry out circumferential ablation on the orifice of the pulmonary vein. That invention is mainly defective in the following aspect: due to the difference in sizes and shapes of the orifices of the patients' pulmonary veins, it is very difficult in practical operation to abut the meshed flat disk completely against the orifice of the pulmonary vein, but instead usually only in a slanting or partial manner, so that it is impossible to carry out ideal circumferential ablation of the orifice of the pulmonary vein, and adversely affecting the therapeutic effect.

SUMMARY OF THE INVENTION

One objective of the present invention is to provide an electrophysiology ablation device that makes possible precise positioning of the ablation electrode at the orifice of the pulmonary vein to carry out precise and ideal circumferential ablation.

Another objective of the present invention is to provide an electrophysiology ablation device, whose ablation electrode is adjustable as to size according to the size of the orifice of the pulmonary vein, so as to abut the ablation electrode against the orifice of the pulmonary vein in a proper size to carry out ideal circumferential ablation.

The objectives of the present invention are realized by an electrophysiology ablation device, which comprises: a catheter sleeve; an electrically conductive electrode sleeve, sheathed inside the catheter sleeve and axially moveable relative to the catheter sleeve; a guiding ball sleeve, sheathed inside the electrode sleeve and axially moveable relative to the electrode sleeve; a central rod, sheathed inside the guiding ball sleeve and axially moveable relative to the guiding ball sleeve; an electrically conductive ablation electrode, connected with one end thereof to a front end of the electrode sleeve and with another end thereof to the guiding ball sleeve, and so configured that, when the two ends thereof are stretched towards directions away from each another, a portion between the two ends is formed into a strip shape capable of being received inside the catheter sleeve, and when the two ends thereof are retracted towards directions approaching each another, the portion between the two ends is formed into a radially deployable meshed disk capable of abutting against the orifice of a pulmonary vein; and a guiding ball, connected with one end thereof to a front end of the guiding ball sleeve and with another end thereof to the central rod, and so configured that, when the two ends thereof are stretched towards directions away from each another, a portion between the two ends is formed into a strip shape capable of being received inside the catheter sleeve, and when the two ends thereof are retracted towards directions approaching each another, the portion between the two ends is radially deployed into a meshed spherical shape, and a center of the meshed guiding ball is disposed on a central axis of the disk ablation electrode.

In the present invention, the ablation electrode is radially deployed into a meshed bowl-shaped disk, wherein a bowl edge is oriented towards the front end of the guiding ball sleeve.

In the present invention, a size of the bowl edge of the deployed meshed bowl-shaped disk is adjustable through adjustment of the relative positions between the electrode sleeve and the guiding ball sleeve.

The ablation electrode is braided from a memory alloy metal wire and provided with an electrically conductive coating.

In the present invention, the guiding ball is braided from a memory alloy metal wire.

In the present invention, a front end of the central rod is connected with a catheter head.

In the present invention, the guiding ball is connected to the catheter head, thereby is connected with the central rod.

In the present invention, a guiding ring is provided at a front end of the catheter sleeve, and a guiding steel wire is inserted through the catheter sleeve with a front end thereof connected to the guiding ring, wherein the direction for which the catheter head is heading can be controlled by the guiding steel wire, so as to make it convenient for the catheter head to pass through the blood vessel.

In the present invention, the guiding ball is opaque under Roentgen ray, thus facilitating observation of the position of the guiding ball during a surgical operation.

In the present invention, the guiding ball is coated with an anticoagulation coating to avoid formation of thrombus due to long duration of the surgical operation.

In the present invention, a control handle is provided at a rear end of the catheter sleeve, wherein the control handle is provided with operational buttons respectively controlling positions of the central rod, the guiding ball sleeve, and the electrode sleeve.

In the present invention, a diameter of the spherical shape upon radial deployment of the guiding ball is substantially equal to a diameter of the pulmonary vein.

By employment of the electrophysiology ablation device according to the present invention, when the catheter reaches the left atrium, the guiding ball and the ablation electrode are sequentially deployed through adjustment of the relative positions of the electrode sleeve, the guiding ball sleeve and the central rod. Since the guiding ball is of a spherical shape and the spherical center is located on the central axis of the disk ablation electrode, the guiding ball more easily slides into the orifice of the pulmonary vein on contact with a peripheral area of the orifice of the pulmonary vein than a common catheter head does, and guides the electrophysiology catheter and the ablation electrode in form of a meshed bowl-like disk to enter the pulmonary vein to thereby help the surgeon more quickly determine the position of the orifice of the pulmonary vein. After the guiding ball enters the orifice of the pulmonary vein, since the circle centers of the guiding ball and the ablation electrode in form of a meshed bowl-like disk are located on the same central axis, and since the diameter of the guiding ball is substantially equal to the diameter of the pulmonary vein, jittering of the electrophysiology catheter in the pulmonary vein can be reduced, and the edge of the meshed bowl-like ablation electrode can be more compactly abutted against the orifice of the pulmonary vein than that of a conventional flat ablation electrode, thereby achieving precise and ideal circumferential ablation once the power is turned on. After ablation, the meshed bowl-like disk ablation electrode serves as a mapping electrode to collect electrical signals coming from the ablated site to map the ablation effect.

SPECIFIC EMBODIMENTS FOR CARRYING OUT THE INVENTION

As shown in FIGS. 1-5, the electrophysiology ablation device according to the present invention comprises such components as a catheter sleeve 1, an electrically conductive electrode sleeve 2, a guiding ball sleeve 4, a central rod 6, an ablation electrode 3, and a guiding ball 5. The electrode sleeve 2 is made of an electrically conductive material and sheathed inside the catheter sleeve 1, the guiding ball sleeve 4 is sheathed inside the electrode sleeve 2, and the central rod 6 is sheathed inside the guiding ball sleeve 4. The catheter sleeve 1, the electrically conductive electrode sleeve 2, the guiding ball sleeve 4 and the central rod 6 are coaxially sheathed together to form the catheter structure, and the catheter sleeve 1, the electrically conductive electrode sleeve 2, the guiding ball sleeve 4 and the central rod 6 are axially moveable relative to one another. The relative axial movement can be relative axial sliding movement amongst these components.

Figure 1:
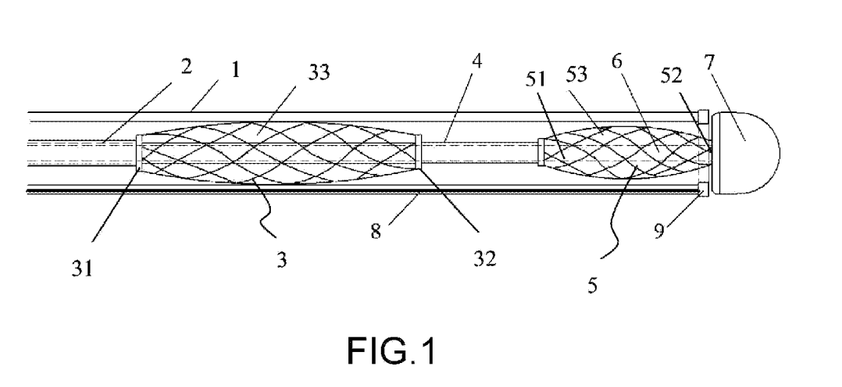
FIG. 1 is a structural view exemplarily illustrating the ablation electrode and the guiding ball placed inside the catheter sleeve according to the present invention.
Figure 2:
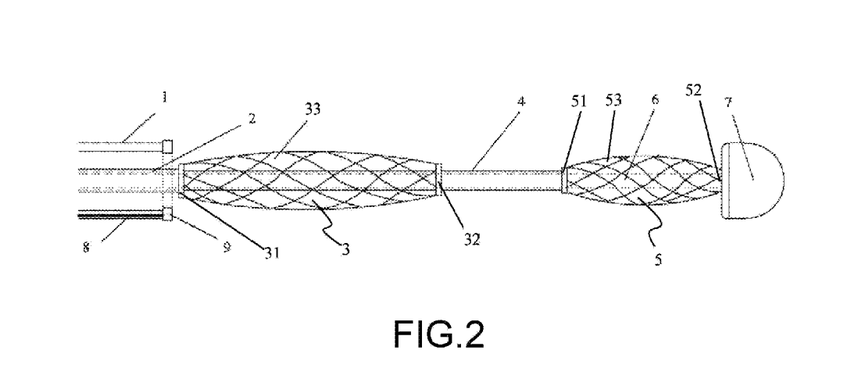
FIG. 2 is a structural view exemplarily illustrating the ablation electrode and the guiding ball protruding out of the catheter sleeve according to the present invention.
Figure 3:
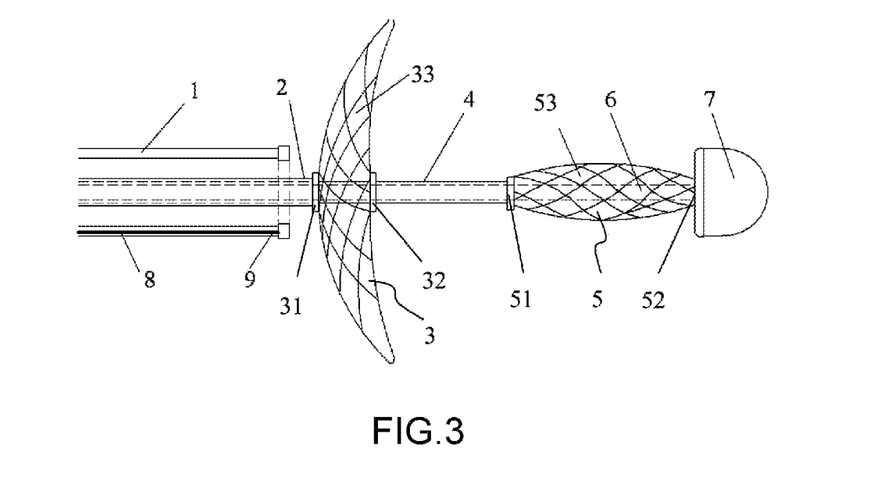
FIG. 3 is a structural view exemplarily illustrating the ablation electrode radially deployed into a disk shape according to the present invention.
Figure 4:
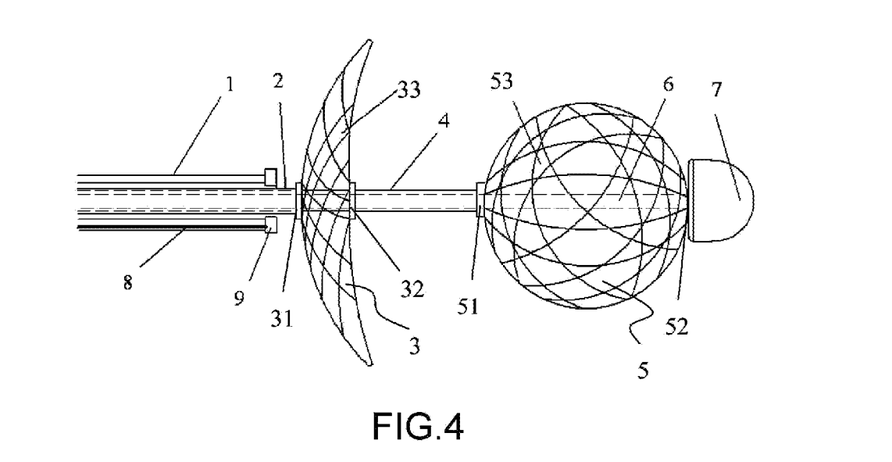
FIG. 4 is a structural view exemplarily illustrating the guiding ball radially deployed into a spherical shape according to the present invention.

One end 31 of the ablation electrode 3 is connected to the front end of the electrode sleeve 2, and another end 32 thereof is connected to the guiding ball sleeve 4. Moreover, the ablation electrode 3 is so configured that, when its two ends 31, 32 are stretched towards directions away from each another, a portion 33 between the two ends of the ablation electrode 3 is formed into a strip shape (as shown in FIGS. 1 and 2) receivable inside the catheter sleeve 1, and when its two ends 31, 32 are retracted towards directions approaching each another, the portion 33 between the two ends of the ablation electrode 3 is radially deployed into a meshed disk (as shown in FIGS. 3 and 4) capable of abutting against the orifice of a pulmonary vein. Since the two ends 31, 32 of the ablation electrode 3 are respectively connected to the electrode sleeve 2 and the guiding ball sleeve 4, the distance between the two ends 31, 32 of the ablation electrode 3 can be adjusted through adjustment of the axial relative positions between the electrode sleeve 2 and the guiding ball sleeve 4, so that the ablation electrode 3 can be transformed between the strip shape and the radially deployed disk shape on demand.

One end 51 of the guiding ball 5 is connected to the front end of the guiding ball sleeve 4, and another end 52 thereof is connected to the central rod 6. Moreover, the guiding ball 5 is so configured that, when its two ends 51, 52 are stretched towards directions away from each another, a portion 53 between the two ends of the guiding ball 5 is formed into a strip shape (as shown in FIGS. 1-3) receivable inside the catheter sleeve 1, and when its two ends 51, 52 are retracted towards directions approaching each another, the portion 53 between the two ends of the guiding ball 5 is radially deployed into a meshed spherical shape (as shown in FIG. 4), and the center of the meshed guiding ball 5 is located on the central axis of the meshed bowl-shaped disk ablation electrode 3. Since the two ends 51, 52 of the guiding ball 5 are respectively connected to the guiding ball sleeve 4 and the central rod 6, when the guiding ball sleeve 4 and the central rod 6 perform relative axial sliding movement, the distance between the two ends 51, 52 of the guiding ball 5 varies accordingly, and the guiding ball 5 is transformed between the strip shape receivable inside the catheter sleeve 1 and the radially deployed spherical shape on demand through adjustment of the relatively axially moved positions between the guiding ball sleeve 4 and the central rod 6. As shown in FIGS. 1-5, after the catheter enters the left atrium, the ablation electrode 3 and the guiding ball 5 are sequentially radially deployed through adjustment of the relative axial positions of the electrode sleeve 2, the guiding ball sleeve 4 and the central rod 6. Since the guiding ball 5 is of a meshed spherical shape having a relatively large curvature radius and the spherical center is located on the central axis of the disk ablation electrode 3, the guiding ball 5 more easily slides into the orifice of the pulmonary vein on contact with a peripheral area of the orifice of the pulmonary vein than a common catheter head does, and guides the electrophysiology catheter and the disk shaped ablation electrode 3 to enter the pulmonary vein to thereby help the surgeon more quickly determine the position of the orifice of the pulmonary vein, thus making it possible to perform relatively ideal circumferential ablation on the orifice of the pulmonary vein, and improving the surgical effect.

Figure 5:
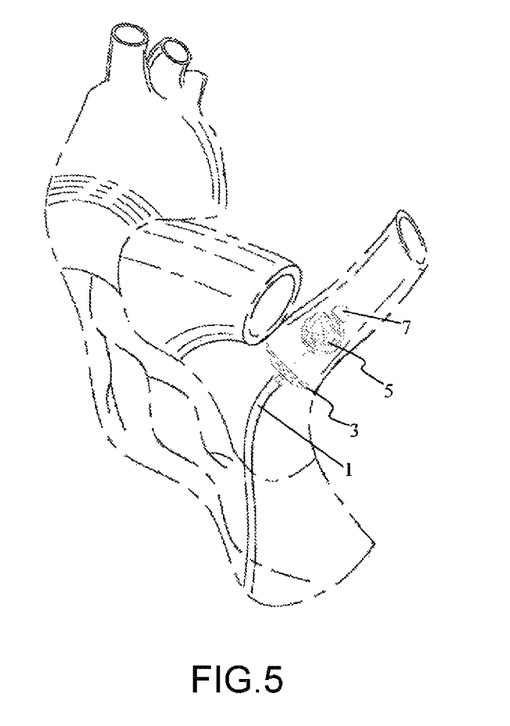
FIG. 5 is a view exemplarily illustrating the state of the electrophysiology ablation device being inserted into the pulmonary vein according to the present invention.

In the present invention as shown in FIG. 5, as an optional concrete example, the diameter of the spherical shape upon radial deployment of the guiding ball 5 is substantially equal to the diameter of the pulmonary vein, jittering of the electrophysiology catheter in the pulmonary vein can be reduced, and the edge of the meshed ablation electrode can be more compactly abutted against the orifice of the pulmonary vein.

In the present invention, the meshed disk that forms the ablation electrode 3 can assume the flat disk of U.S. Pat. No. 6,837,886 B2, and can also assume any other disk shape, as long as the disk can contact with the site peripheral to the orifice of the pulmonary vein to function for circumferential ablation. As an optional embodiment shown in FIGS. 3-4, the ablation electrode 3 can be radially deployed into a meshed bowl-shaped disk, wherein the bottom of the bowl is oriented towards the front end of the electrode sleeve 2. The diameter of the meshed bowl-like disk ablation electrode 3 is adapted to the size of the orifice of the pulmonary vein of a patient observed during the surgical operation through adjustment of the relative axial positions between the electrode sleeve 2 and the guiding ball sleeve 4, so that, after the guiding ball 5 enters the orifice of the pulmonary vein, the edge of the meshed bowl-like disk, which is coaxial with the guiding ball 5, can be more compactly abutted against the orifice of the pulmonary vein than that of a conventional flat disk (such as the flat disk in U.S. Pat. No. 6,837,886 B2), thereby achieving precise and ideal circumferential ablation once the power is turned on.

In the present invention, the ablation electrode 3 can be braided from a memory alloy metal wire and provided with an electrically conductive coating, to guarantee formation of the needed meshed bowl-like disk upon radial deployment. The guiding ball 5 is also braided from a memory alloy metal wire to guarantee formation of the meshed spherical shape upon radial deployment.

In the present invention as shown in FIGS. 1-5, the front end of the central rod 6 is connected with a catheter head 7 functioning to guide during the process the catheter enters the left atrium. For the central rod 6 connected with the catheter head 7, the front end 52 of the guiding ball 5 can be directly connected to the catheter head 7 to thereby form connection with the central rod 6.

As shown in FIGS. 1-5, a guiding ring 9 is provided at the front end of the catheter sleeve 1, and a guiding steel wire 8 is inserted through the catheter sleeve 1 with a front end thereof connected to the guiding ring 9. The catheter sleeve 1, the electrode sleeve 2, the guiding ball sleeve 4 and the central rod 6 are flexible to allow the catheter to pass through the blood vessel. As shown in FIG. 1, before the guiding ball 5 and the ablation electrode 3 protrude out of the catheter sleeve 1, the catheter head 7 is closely abutted against the guiding ring 9, and the direction for which the catheter head 7 is heading can be controlled by tightly pulling the steel wire 8 to let it bend, so as to facilitate its passing through the blood vessel.

In the present invention, the guiding ball 5 is opaque under Roentgen ray, thus facilitating observation of the position of the guiding ball 5 during a surgical operation. The guiding ball 5 can also be coated with an anticoagulation coating to avoid formation of thrombus due to long duration of the surgical operation.

Figure 6:
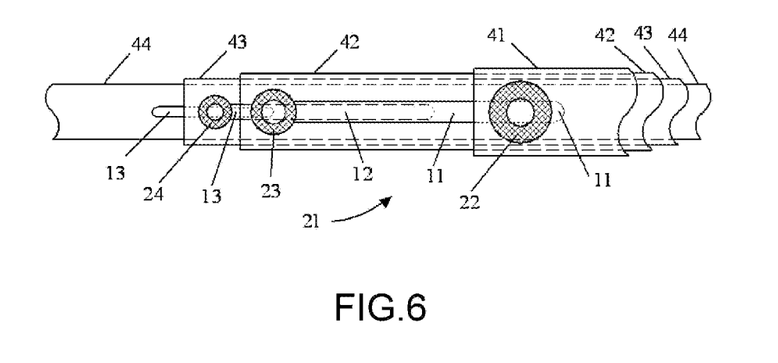
FIG. 6 is a view exemplarily illustrating an optional structure of the control handle of the electrophysiology ablation device according to the present invention.

As shown in FIG. 6, to facilitate control of the relative axial positions amongst the electrode sleeve 2, the guiding ball sleeve 4 and the central rod 6, a control handle 21 is provided at a rear end of the catheter sleeve 2, and the control handle 21 is provided with operational buttons respectively controlling the relative axial positions amongst the central rod 6, the guiding ball sleeve 4, and the electrode sleeve 2. As an optional embodiment for the control handle 21 shown in FIG. 6, the control handle 21 comprises (but not limited to) a bushing 41, a bushing 42, a bushing 43, a bushing 44, a button 22, a button 23, a button 24 (that constitute the aforementioned operational buttons), and a slide groove 11, a slide groove 12, a slide groove 13 each disposed on a respective bushing. Release of the button 22 causes the bushing 41 and the bushing 42 to slide relative to each other, release of the button 23 causes the bushing 42 and the bushing 43 to slide relative to each other, and release of the button 24 causes the bushing 43 and the bushing 44 to slide relative to each other. The bushing 41 is connected to the catheter sleeve 1, the bushing 42 is connected to the electrode sleeve 2, the bushing 43 is connected to the guiding ball sleeve 4, and the bushing 44 is connected to the central rod 6, so that such connections are flexible connections (the so-called flexible connections indicate the connections can be bended, however, the connections can neither be axially elongated along the connecting axis nor axially contracted along the connecting axis), and should guarantee the following distances to be equal: the relative distance between the moveable bushing 41 and bushing 42 is equal to the relative distance between the moveable catheter sleeve 1 and electrode sleeve 2, the relative distance between the moveable bushing 42 and bushing 43 is equal to the relative distance between the moveable electrode sleeve 2 and guiding ball sleeve 4, and the relative distance between the moveable bushing 43 and bushing 44 is equal to the relative distance between the moveable guiding ball sleeve 4 and central rod 6. But this does not mean that the bushing 41 equals the catheter sleeve 1 in diameter, that the bushing 42 equals the electrode sleeve 2 in diameter, that the bushing 43 equals the guiding ball sleeve 4 in diameter, and that the bushing 44 equals the central rod 6 in diameter, as the diameters of these can either be equal or unequal to one another, to which no definition is made here. Of course, the handle 21 may further comprise the guiding steel wire 8, various electric buttons to control ablation and mapping, and some other buttons and structures as deemed necessary. However, these are either inconsequential or irrelevant to the present invention, are not marked up in the drawings, and are not described in detail here.

The specific structure of the control handle 21 may also assume the structure in U.S. Pat. No. 6,837,866 B2, or any other such structures as with regulation nuts respectively provided therebetween, by rotation of which regulation nuts the axial positions therebetween can be adjusted, and such specific structures are not restricted insofar as it is possible to control the relative axial positions between the guiding ball sleeve 4 and the electrode sleeve 2.

In the present invention, all of the aforementioned front end indicates the end that is close to the catheter head 7. In the present invention, the electrode sleeve 2 and the ablation electrode 3 are electrically conductive, while the catheter head 7, the guiding ball 5 and the remaining sleeves are not electrically conductive. As shown in FIG. 1, the guiding ball 5 and the ablation electrode 3 are both concealed inside the catheter sleeve 1 prior to deployment.

With reference to FIGS. 1-6, the specific process of using and operating the electrophysiology ablation device according to the present invention is described as follows:

1) the catheter is firstly delivered to the left atrium in a conventional artery puncture mode (as shown in FIG. 1, at this time both the guiding ball 5 and the ablation electrode 3 are concealed inside the catheter sleeve 1), the buttons 22, 23, 24 are then released, the central rod 6 is urged forward, the guiding ball sleeve 4 and the electrode sleeve 2 both protrude out of the catheter sleeve 1 under the pulling action of the guiding ball 5 and the ablation electrode 3, and the electrode sleeve 2 is locked-in by means of the button 22 on the control handle 21 so that its position is fixed relative to the catheter sleeve 1 (as shown in FIG. 2);

2) the guiding ball sleeve 4 is pulled back and locked-in by means of the button 23, so that the two ends 31, 32 of the ablation electrode 3 are retracted towards directions approaching each other, and the ablation electrode 3 is radially deployed into a meshed bowl-like disk, the size of the bowl edge being controlled through adjustment of the relative positions of the guiding ball sleeve 4 and the electrode sleeve 2 (as shown in FIG. 3);

3) the central rod 6 is pulled back, and the button 24 on the control handle 21 is locked-in, so that the guiding ball 5 is radially deployed into a meshed spherical shape (as shown in FIG. 4);

4) according to dynamic imaging under Roentgen ray, the catheter head 7 is delivered into the pulmonary vein under guidance of the guiding ball 5, the size of the orifice of the pulmonary vein is observed, the button 23 is released, the diameter of the disk of the ablation electrode 3 is controlled through adjustment of the relative positions of the guiding ball sleeve 4 and the electrode sleeve 2 so that the disk is abutted against the orifice of the pulmonary vein in a proper size (as shown in FIG. 5), and the button 23 is subsequently locked-in;

6) the meshed bowl-like ablation electrode 3 is powered on to perform RF ablation on the orifice of the pulmonary vein;

7) after the ablation is completed, the RF power is turned off, and the ablation switch is switched to the mapping position to use the ablation electrode 3 as a mapping electrode to check the ablation effect; and 8) the catheter head 7 and the bowl-like ablation electrode 3 are retracted to the left atrium, the control button 24 of the central rod 6, the control button 23 of the guiding ball sleeve 4 and the control button 22 of the electrode sleeve 2 on the control handle 21 are sequentially released, the central rod 6 and the guiding ball sleeve 4 are sequentially pushed forward so that the guiding ball 5 and the ablation electrode 3 are pulled again into the strip shape and respectively abutted against the central rod 6 and the guiding ball sleeve 4, and the electrode sleeve 2 is pushed forward again, so that the ablation electrode 3 and the guiding ball 5 are retracted into the catheter sleeve 1, then the catheter sleeve 1 is withdrawn from the human body.

Due to the guiding action of the guiding ball 5 during the process of electrophysiologically ablating the orifice of the pulmonary vein with the electrophysiology ablation device according to the present invention, the surgical operator can relatively quickly determine the position of the orifice of the pulmonary vein to precisely position the ablation electrode 3. Since the ablation electrode 3 is of a meshed bowl-like disk with the blow edge being adjustable as to size according to the size of the orifice of the pulmonary vein, the ablation electrode 3 can be abutted against the orifice of the pulmonary vein in a proper size. Therefore, the electrophysiology ablation device according to the present invention can carry out precise and ideal circumferential ablation, and greatly improve the effect of electrophysiology ablation surgery.

The invention claimed is:

1. An electrophysiology ablation device, comprising:
a catheter sleeve;
an electrically conductive electrode sleeve, sheathed inside the catheter sleeve and axially moveable relative to the catheter sleeve;
a guiding ball sleeve, sheathed inside the electrode sleeve and axially moveable relative to the electrode sleeve;
a central rod, sheathed inside the guiding ball sleeve and axially moveable relative to the guiding ball sleeve;
an electrically conductive ablation electrode, connected with one end thereof to a front end of the electrode sleeve and with another end thereof to the guiding ball sleeve, and so configured that, when the two ends thereof are stretched towards directions away from each other, a portion between the two ends is formed into a strip shape capable of being received inside the catheter sleeve, and when the two ends thereof are retracted towards directions approaching each other, the portion between the two ends is radially deployed into a meshed disk capable of abutting against the orifice of a pulmonary vein; and
a guiding ball, connected with one end thereof to a front end of the guiding ball sleeve and with another end thereof to the central rod, and so configured that, when the two ends thereof are stretched towards directions away from each other, a portion between the two ends is formed into a strip shape capable of being received inside the catheter sleeve;
characterized in that the guiding ball is so configured that, when the two ends thereof are retracted towards directions approaching each other, the portion between the two ends is radially deployed into a meshed spherical shape with its center being disposed on a central axis of the disk ablation electrode, the guiding ball coated with an anticoagulation coating;
a diameter of the spherical shape upon radical deployment of the guiding ball is substantially equal to a diameter of the pulmonary vein;
wherein, in use, when the catheter reaches the left atrium, the guiding ball and the ablation electrode or the ablation electrode and the guiding ball can be sequentially deployed through adjustment of the relative positions of the electrode sleeve, the guiding ball sleeve and the central rod; and
wherein, in use, since the guiding ball is of a spherical shape and the spherical center is located on the central axis of the disk ablation electrode, the guiding ball can easily slide into the orifice of the pulmonary vein on contact with a peripheral area of the orifice of the pulmonary vein, so as to guide the electrophysiology catheter and the ablation electrode.

2. The electrophysiology ablation device according to claim 1, characterized in that the ablation electrode is radially deployed into a meshed bowl-shaped disk, wherein a bowl edge is oriented towards the front end of the guiding ball sleeve.

3. The electrophysiology ablation device according to claim 2, characterized in that a size of the bowl edge of the ablation electrode deployed into a meshed bowl-shaped disk is adjustable.

4. The electrophysiology ablation device according to claim 1, characterized in that the ablation electrode is braided from a memory alloy metal wire and provided with an electrically conductive coating.

5. The electrophysiology ablation device according to claim 1, characterized in that the guiding ball is braided from a memory alloy metal wire.

6. The electrophysiology ablation device according to claim 1, characterized in that a front end of the central rod is connected with a catheter head.

7. The electrophysiology ablation device according to claim 6, characterized in that the guiding ball is connected to the catheter head, thereby being connected with the central rod.

8. The electrophysiology ablation device according to claim 1, characterized in that a guiding ring is provided at a front end of the catheter sleeve, and that a guiding steel wire is inserted through the catheter sleeve with a front end thereof connected to the guiding ring.

9. The electrophysiology ablation device according to claim 1, characterized in that the guiding ball is opaque under Roentgen ray.

10. The electrophysiology ablation device according to claim 1, characterized in that a control handle is provided at a rear end of the catheter sleeve, wherein the control handle is provided with operational buttons respectively controlling positions of the central rod, the guiding ball sleeve, and the electrode sleeve.

\* \* \* \* \*